United States Patent
Francis et al.

(10) Patent No.: US 8,666,775 B2
(45) Date of Patent: Mar. 4, 2014

(54) BUSINESS METHOD AND SYSTEM FOR PROVIDING A HEALTH SECURITY ORGANIZATION FOR PROCURING AND FINANCING HEALTHCARE PRODUCTS AND SERVICES

(76) Inventors: Daniel Paul Francis, Dawsonville, GA (US); Richard E Jung, Nashville, TN (US)

( * ) Notice: Subject to any disclaimer, the term of this patent is extended or adjusted under 35 U.S.C. 154(b) by 0 days.

(21) Appl. No.: 13/451,863

(22) Filed: Apr. 20, 2012

(65) Prior Publication Data
US 2012/0203568 A1 Aug. 9, 2012

Related U.S. Application Data

(63) Continuation-in-part of application No. 12/485,240, filed on Jun. 16, 2009, now abandoned.

(51) Int. Cl.
*G06Q 40/00* (2012.01)

(52) U.S. Cl.
USPC .................................. 705/2; 705/3

(58) Field of Classification Search
USPC ............................................. 705/2
See application file for complete search history.

(56) References Cited

U.S. PATENT DOCUMENTS

| | | | | |
|---|---|---|---|---|
| 5,950,175 | A * | 9/1999 | Austin | 705/36 R |
| 7,254,555 | B2 * | 8/2007 | Field | 705/36 R |
| 8,000,977 | B2 * | 8/2011 | Achan | 705/2 |
| 8,316,005 | B2 * | 11/2012 | Moore | 707/707 |
| 2003/0014351 | A1 * | 1/2003 | Neff et al. | 705/37 |
| 2006/0059078 | A1 * | 3/2006 | Courbois et al. | 705/37 |
| 2008/0091579 | A1 * | 4/2008 | Barrett | 705/34 |
| 2008/0167901 | A1 * | 7/2008 | Betz | 705/2 |
| 2008/0319787 | A1 * | 12/2008 | Stivoric et al. | 705/2 |
| 2009/0132289 | A1 * | 5/2009 | Stenman et al. | 705/4 |

OTHER PUBLICATIONS

Development of information Security Baseline for Healthcare: Lech Janczeweski et al; Computer & Security,: vol. 21, issue2, Mar. 31, 2002, pp. 172-192.*
Mobile healthcare computing devices . . . patient data delivery: Binshan Lin et al; vol. 2, No. 4/2004, pp. 343-353; Online date— Wednessday, Jan. 5, 2005.*
Towards a practical healthcare information security model for healthcare institutions: Dwivedi, A et al:Published in: Information Technology Application in Biomedicine, 2003, 4th International IEEE EMBS Special Topic Conference on: Apr. 24-26, 2003.*

* cited by examiner

*Primary Examiner* — Hani M Kazimi
*Assistant Examiner* — Hatem M Ali
(74) *Attorney, Agent, or Firm* — Richard Jung-Agent

(57) ABSTRACT

A Health Security Organization (HSO) service method and system provides healthcare service vouchers which allow an individual or an entity to purchase and store shares which correlate to CPT (Common Procedural Terminology) codes and are exchangeable for healthcare purposes. The shares can be purchased individually or in bulk packages and are transferable through a provider or provisionary of healthcare needs including pharmaceuticals. The shares are transferable, non-expiring, and usable at any health care provider willing to exchange the shares for currency in a similar fashion to an exchange of services with an insurance or credit card holder. The share transfer provides immediate payment for services rendered. Additionally, the cards can be utilized in such a fashion that if repetitive services are needed they can be acquired in a more economical method via bulk purchasing. Share transfers are redeemed by a member and provider via internet accessible computer system.

9 Claims, 11 Drawing Sheets

20

Capacity of services a provider can deliver on any single day is a significant piece of information as the baby boomer population comes into retirement. This is the basis for the shares.
Then you divide the cost of these services

| Cost of those services at any point in time divided by Number of services available | = | Shares available for sale at any location at any particular point in time |

BUSINESS METHOD AND SYSTEM FOR PROVIDING A HEALTH SECURITY ORGANIZATION FOR PROCURING AND FINANCING HEALTHCARE PRODUCTS AND SERVICES

RELATED APPLICATIONS

This application is a continuation-in-part and claims the benefit of the prior nonprovisional application Ser. No. 12/485,240 filed on Jun. 16, 2009 now abandoned.

FIELD OF THE INVENTION

The present invention generally relates to a method and system for implementing a health security organization to serve as a medium through which patients may procure rights to services of healthcare providers of all types. More specifically, the present invention relates to a business model method and apparatus for providing an alternative to health insurance, while maintaining coverage by offering a service procurement an payment format.

BACKGROUND OF THE INVENTION AND RELATED ART

Since the advent of the stock market, people have become familiar with the benefits of owning publicly traded stocks—ownership in companies. However, while this concept has been employed successfully in the context of business ownership, it has not bridged the gap to the services sector of the economy. There currently exists no means for a consumer to purchase shares representing healthcare services. Further problems confronting a consumer willing to purchase these shares include: convenient means for verifying a provider's qualifications; a method or medium for redeeming shares for medical services; available packages or levels of access to be customized for individual's needs.

In this regard, there exists a need to provide a consumer with a convenient, cost effective alternative for healthcare coverage. Furthermore, consumers need an environment in which they have more control of their coverage, specifically the cost of desired services.

SUMMARY OF THE INVENTION

The illustrative exemplary non-limiting implementation described herein provides a comprehensive health security organization for providing a method and system of providing payment to healthcare providers for rendered healthcare services.

A Health Security Organization (HSO) is a unique medical service system. The HSO is a service procurement and payment format of electronically connected value system connected through an electronic portal to healthcare provides. The HSO provides access to care, research on providers of all types, data capture in a unique database, and scheduling services for the consumer. The HSO model provides payment at the time of service in a retail format consisting of a transaction that occurs in the providers' place of business via their merchant account or "credit card machine" and is called a "cash" transaction.

The HSO has several unique features that include: A provider database, an online point of sale system for providers, different levels of access, Health Care Shares, a Health Care Broker, Health Care Shareholder, account Key Holder, and the Voucher that represents the Health Care Shares at the time of a transaction.

The Health Care Shares are a universal currency in the health care marketplace and can be redeemed for any service at any time for any reason the key holder of the account deems appropriate. The person that buys the shares is called a Shareholder. The shares are currently represented in a funds to share ratio of 1:1, this is not intended to be a permanent representation and the ratio is subject to adjustment based on market conditions at any given time. The shares are used to purchase health care products from providers, insurance companies and other health related retail organizations. They are called shares as a result of the finite number of services available to the general population; they are purchasing a share of that finite quantity.

The model is exercised when a consumer who enrolls into the HSO seeks health care service from the community at large and engages our health care agents and other professionals to search for services, negotiate pricing and scheduling, and book the appointment. The consumer will then see the provider and the provider will demand and receive payment via this format.

The quantity of shares available is determined by a formula that represents all available services in the United States or any other country that the system is in place and available. The formula is:

Number of services available×cost of those services=shares available

For example, a provider can see 30 people a day at $100 dollars each=3000 shares a day can be redeemed by this provider, or, 3000 shares a day could be sold to see this provider, but either way, the total number of shares available to redeem through this provider daily is 3000.

There are 500,000 primary care providers in the USA. If all of them had the same capacity as the example there would be 1.5 billion shares available for sale or redemption on any given day relative to primary care providers.

Health Care Shares never expire. They may lose or gain buying power depending on market conditions, availability of services, geographical location of the consumer, or government regulation. They are transferable from one member to another. The shares are purchased from a Health Care Broker via the electronic interface, which is the definition of this company as it is positioned in this model. The Broker determines the available base of health care services and establishes the Suggested Retail Price of all goods and services. The Broker's primary purpose is to be the pinnacle monitor of the system at large and make services available to the systems members to ensure they have access to the health care good and services they desire while managing the database and funds in a manner that makes them available at all times to the member or members provider for information and payment at the time of service. In addition to this primary role, the broker also endeavors to enhance the buying power of the shareholders with provider through negotiating bulk rate pricing for the members. The Broker additionally trains the providers into this method of payment and encourages the provider to adapt the Retail Medical Home Model as their method of operation to ensure access to the shareholders, reduce costs to shareholders and to offer a comprehensive care approach. The broker does not choose providers for the shareholder. The Broker does not make any medical suggestions or recommendations for care to the shareholder. The broker facilitates the relationship between the provider and the shareholder. The Shareholder can redeem their shares by presenting the voucher representation to the provider as a means of transferring payment form the Brokers trust account to the provider for services rendered. The Shareholder is free to choose any provider they believe will best meet their needs. The Shareholder may also contact a Health Care Agent who works for the Broker and is a professional health care buyer if they want assistance or are seeking a better price on the service they need. This agent may be an employee, contractor, or other organization or person that is qualified or certified by the Broker to provide such services. The Health Care Voucher is designed as the device that contains instructions for use (redemption), including how to locate a provider. The Voucher represents the account of the shareholder.

Health Care providers in this model are considered any licensed provider of service the shareholder deems qualified to meet their need(s). There are no restrictions or conditions on this choice as the shareholder may choose a licensed provider, which may be a medical, dental, veterinary, or other, to address their personal needs. Unlike an insurance company, the broker does not control pricing, care protocols, or patient care. The types of services are categorized under virtual storefronts called Access Levels (Access). The Access level determines the type of shares being purchased. The Access levels are broken into categories such as primary care, specialty care, hospital/surgical, et. al. The Access Levels are also connected to the provider Database. This is the space on the internet or otherwise, that is maintained by the Broker for the purpose of profiling providers based on their historical transactions with the broker. The Shareholder can view this information as needed to assist in selecting a provider. The profile may contain but is not limited to data pertaining to cost of services, availability of the provider, scope of care at the provider practice, official complaints to professional boards, Medical Home status, and other criteria as determined by the Broker to be pertinent. This information is made available via the internet and call center representatives to the shareholders to further assist them in making provider selections. The data is available on the internet twenty-four hours a day.

Any health care consumer can buy health care shares, including; government, individuals, businesses, organizations, and associations. The shares are stored in a database file structure that is monitored and maintained by the Broker. The shares can only be used for health care services as identified and desired by the Shareholder. The share purchase and issue process entails the creation of an account and the provision of an account number. A voucher identifier is then issued along with a physical representation, which may be but is not limited to a plastic card, paper document, an electronic device, or a virtual representation or device. The consumer then purchases a level of access, i.e. primary care or hospitalization, to identify the level they wish to participate; the consumer also has the option of placing shares in general access where they can be used for any purpose. The shareholder can now purchase pre-defined blocks of shares called "Share Banks" Share banks represent a bulk purchase of shares and can be bought in a number of different formats including but not limited to monthly plans where the shareholder is on a scheduled monthly purchase option. The monthly plans come in different quantity packages of shares such as the Bronze plan that purchases 175 shares per month. They can buy a single share bank per year, on any date of their choosing the shareholder can purchase the amount of shares they expect to need for the following year, and intermittent installment where the shareholder is randomly purchasing blocks of shares for the account on no set schedule. The shares are stored in the data file and can be used by the shareholder at a later time for services received. The levels of access and shares can be purchased by the shareholder or potential shareholder by going to the brokers website or calling the broker and ordering by phone or by visiting in any location a broker representative that is authorized by the broker to sell the shares. There is no limit to the number of shares that can be purchased, except the maximum amount of shares that are available according to the formula used to determine the quantity of shares the market during any given time period. The shares never expire but may lose purchasing power as market conditions change and pricing from providers change or the shareholder changes their geographical location. The shares may gain purchasing power as the market determines as well due to technological advances, greater availability of a service, reduction in provider pricing, and/or greater influence of the Broker Trust on a local market.

The funds generated for share purchases are deposited into an insured financial institution. The individuals share purchase and contributions to this fund are monitored and controlled by the broker via the data file system. Providers access the fund for payment via call in transactions or via the internet Point of Sale system provided by the Broker.

The shareholder buys the shares and the broker deposits the funds into a restricted commercial bank account. The broker then removes from the purchase any associated fees and costs, then deposits the remaining funds into the Shareholder Trust Account. This is unlike an HSA as all funds are deposited into a single account and the monitoring of the individual shareholders funds is achieved via the data file system maintained by the Broker. The data required from the shareholder is designed to protect anonymity without restricting the ability to retrieve information from the database. The shareholder must provider their Name, Date of Birth and zip code of residence to access their account along with controlled information i.e. an account number provided by the broker, to guarantee access to the information. Upon receipt of this information the Broker can verify the account as valid and active with sufficient balance to cover the services being sought that day. The consumer can decide if they want to remain anonymous and add security features that will allow the Broker to identify the Shareholder without a name or other common identifying information. The Broker will establish a number sequence that can only be completed by the shareholder as a method of access along with other security measures. The Shareholder can allow others to use the account if the Shareholder is also the Key Holder of the account. The Key Holder can contact the Broker and add the new Shareholder to their account for periods of one month at a time or for an indefinite period of time. The choice to add a shareholder to an account is exclusively the Key Holders decision; the Broker does not influence this decision.

Once the Broker has identified the individuals that will be on an account under a single key holder, they can choose an access level(s) they wish to participate in. Access levels are designed to allow a single individual to purchase specific products from the marketplace that they deem necessary for their well being. This could be Primary Care services, a membership to a medical home, specialty care, surgical care, or hospital care amongst many others. Access levels serve different purposes in the model. The main function of an access level is to act as a budgetary guideline for the consumer, so the shareholder can look into where they are spending their health care shares and what value they perceive from the care they have received. A secondary benefit of access levels is the data compiled in the data file that can be used to forecast and report utilization patterns and available funds for a specific type of care. If funds are available to a pre determine level in a specific geographical area, the Broker may choose to offer a "Group Visit", or health Care Fair to the members in that area to better serve their health care needs. The Broker arranges these services and purchases them up front and then resells the service to the members at a discounted rate. The benefit to the shareholder is guaranteed, the benefit to the broker will be determined based on sales or the program to the shareholders. Access levels also identify virtual storefronts for the evaluation and purchasing of shares.

Once a Shareholder has the voucher and has selected their desired level of access they can load their voucher account with services, or leave the shares as a stand-alone product to only be redeemed at the time they seek services. This is not a pre-paid medical service as the transaction actually occurs between the provider and the Broker at the time of service. This process is a unique health care equity system that allows the shareholder to gain buying power by selecting service packages that have been made available from a variety of sources including but not limited to the broker, the providers, the shareholders, an insurance group, employer, government entity, or an insurance group. The Shareholder can also choose a provider at the Brokers website and view the transaction history the broker has with that provider to assist in making choices of which providers to use for the needs. The Shareholder can choose any provider from any source and is not restricted to only using packages that are offered via the above sources.

Once the shareholder is enrolled, purchased access levels, loaded the access levels with shares, contacted a health care agent or searched for a provider on their own and decided to attend to a provider's business and has received services from that provider, they are ready to redeem the shares for payment to the provider for the services rendered. The device (voucher) that represents the shareholders account is presented to the provider or providers' agent, the agent then calls into the transaction center (call center) and gives the required information to the broker representative on the phone. The required information on the shareholder includes but is not limited to: Shareholder date of birth; First and Last initial; Zip code of residence; Common procedural Terminology Codes (CPT Codes); ICD-9 codes; and the total cost as opposed to a fee-per-service cost such as an insurance claim would require.

The Provider's agent can also access payment from the broker trust fund via the online Point of Sale system. The provider will enter their state license number and personal identification number and all the required data from the shareholder in to the provider transaction portion of the Broker website, enter the required information along with banking account information to allow a direct deposit of the payment into the provider bank account, and then submit the data for payment. The data will be electronically reviewed and then payment submitted if all information is deemed correct. The data is kept under the shareholders account as an Electronic Medical Record and can be shared with any provider the shareholder chooses to allow access.

Once the payment has been made and the shareholder data entered the transaction is complete, the shareholder account will be deducted the amount of shares required to make the payment in the database. At this time the shareholder will have a complete interaction and can choose additional services as needed, deposit additional funds as desired or can allow the account to remain static until the shares are needed for redemption.

BRIEF DESCRIPTION OF THE DRAWINGS

These and other features and advantages provided by the exemplary health security organization acquisition and transaction method disclosed herein will be better and more completely understood by referring to the following detailed description of presently preferred embodiments in conjunction with the drawings, of which:

FIG. 2 is a block diagram illustrating how the quantity of available shares for sale or redemption is determined;

DETAILED DESCRIPTION OF EXEMPLARY EMBODIMENTS OF THE INVENTION

A non-limiting description of the exemplary health security organization (HSO) service method and system is provided herein.

Figure 1:
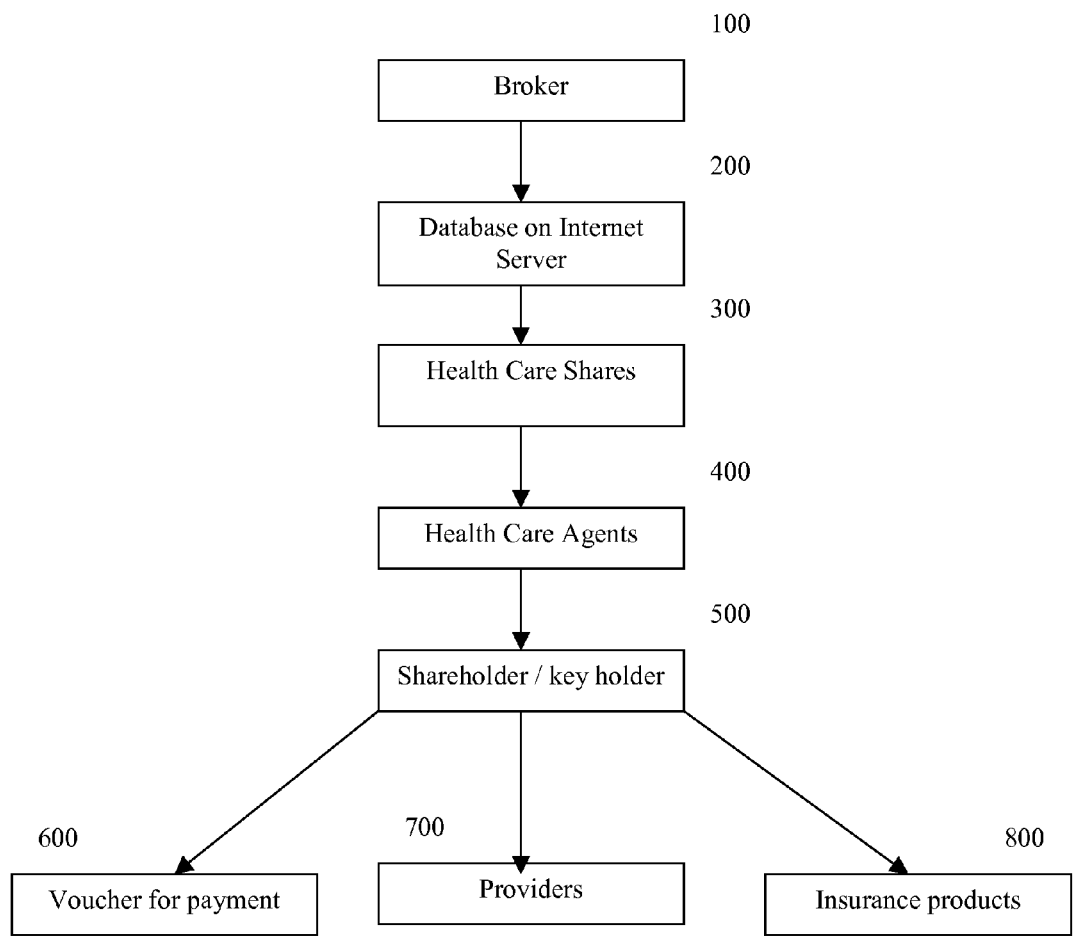
FIG. 1 is a high-level block diagram illustrating the different components of a Health Security Organization.

FIG. 1 is a high-level block diagram illustrating the different components of a Health Security Organization (HSO). The figure simply shows the components, but not the organizational operation. The components of the HSO are: Broker 100, Database on Internet Server 200, Health Care Shares 300, Health Care Agents 400, Shareholder/key holder 500, Voucher for payment 600, Providers 700, and Insurance products 800.

The Broker 100 determines the available base of health care services and establishes the Suggested Retail Price of all goods and services. The Broker's primary purpose is to monitor the system at large and make services available to the systems members to ensure they have access to the health care good and services they desire while managing the database on the internet server 200 and funds in a manner that makes them available at all times to the member or members provider for information and payment at the time of service. In addition to this primary role, the broker also endeavors to enhance the buying power of the shareholders with provider through negotiated exchange of shares for services delivered. The Broker additionally trains the providers into this method of payment and encourages the provider to adapt the Retail Medical Home Model as their method of operation to ensure access to the shareholders, reduce costs to shareholders and to offer a comprehensive care approach. The broker does not choose providers for the shareholder. The Broker does not make any medical suggestions or recommendations for care to the shareholder. The broker facilitates the relationship between the provider and the shareholder.

The Health Care Shares 300 are a universal currency in the health care marketplace and can be redeemed for any service at any time for any reason the key holder of the account deems appropriate. The person that buys the shares is called a Shareholder. The shares are currently represented in a funds to share ratio of 1:1, this is not intended to be a permanent representation and the ratio is subject to adjustment based on market conditions at any given time. The shares are used to purchase health care products from providers, insurance companies and other health related retail organizations. They are called shares as a result of the finite number of services available to the general population; they are purchasing a share of that finite quantity. Health Care Shares never expire. They may lose or gain buying power depending on market conditions, availability of services, geographical location of the consumer, or government regulation. They are transferable from one member to another. The shares are purchased from a Health Care Broker, which is the definition of this company as it is positioned in this model.

The shares are stored in a database file structure that is monitored and maintained by the Broker. When payment for treatment is needed, the data required from the shareholder is designed to protect anonymity without restricting the ability to retrieve necessary information from the database. Once the payment has been made and the shareholder data entered, the transaction is complete. The shareholder account will be deducted the amount of shares required to make the payment in the database.

The Health Care Agent 400 works for the Broker and is a professional health care buyer. This agent may be an employee, contractor, or other organization or person that is qualified or certified by the Broker to provide such services.

The Shareholder 500 can redeem their shares by presenting the voucher representation to the provider as a means of transferring payment form the Brokers trust account to the provider for services rendered. The Shareholder is free to choose any provider they believe will best meet their needs. The Shareholder may also contact the Health Care Agent who works for the Broker and is a professional health care buyer if they want assistance or are seeking a better price on the service they need.

The Health Care Voucher 600 is designed as the device that contains instructions for use (redemption), including how to locate a provider. The Voucher represents the account of the shareholder.

Health Care providers 700 in this model are considered any licensed provider of service the shareholder deems qualified to meet their need(s). There are no restrictions or conditions on this choice as the shareholder may choose a licensed provider, which may be a medical, dental, veterinary, or other, to address their personal needs.

Shares can also be used to purchase health care products 800 from insurance companies and other health related retail organizations.

FIG. 2 is a block diagram illustrating how the quantity of available shares for sale or redemption 20 is determined. The quantity of shares available is determined by a formula that represents all available services in the United States or any other country that the system is in place and available. The formula is: Cost of services/Number of services available (21)=shares available (22). This determination is made for each provider independently. It does not restrict the provider or commit the provider, it is a definition used internally to assure the services promised accessible by the provider. Insurance does not track market availability to ensure services. They promise all things to all members. This is an impossible thing to guarantee. Using this method we actually track the availability of services in any geographic area. And can guarantee service availability when we book the service for the client.

Figure 3:
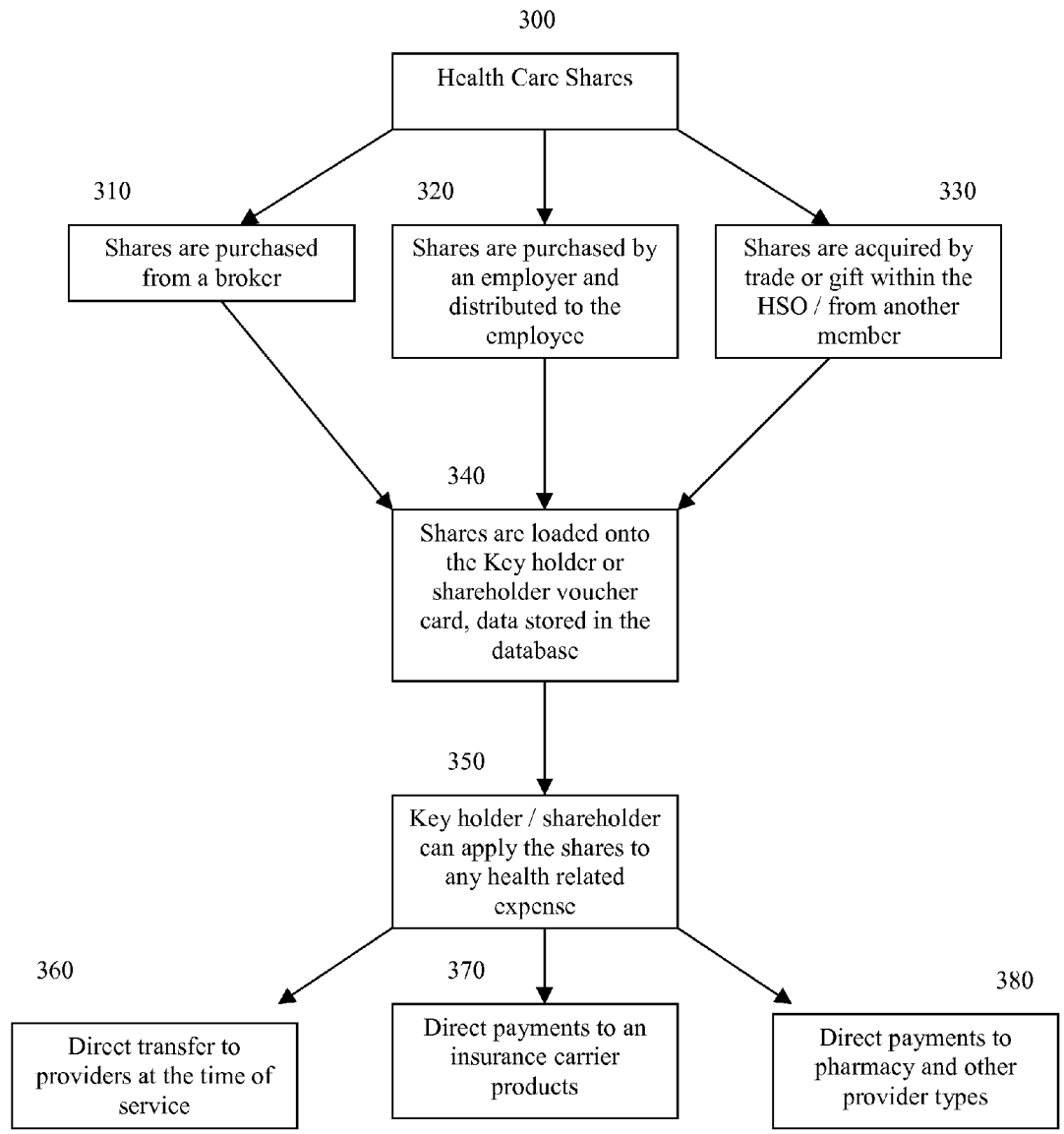
FIG. 3 is a block diagram illustrating the Health Care Share Universal Payment System.

FIG. 3 is a block diagram illustrating the Health Care Share Universal Payment System. Health Care Shares 300 can be purchased from a broker 310, by an employer and distributed to the employee 320, or acquired by trade or gift within the HSO/from another member 330. Shares are loaded onto the Key holder or shareholder voucher card, and data stored in the database 340. The key holder/shareholder can then apply the shares to any health related expense 350 via direct payments to providers during the time of service 360, direct payments to an insurance carrier 370, or direct payments to a pharmacy or other provider types 380.

Figure 4:
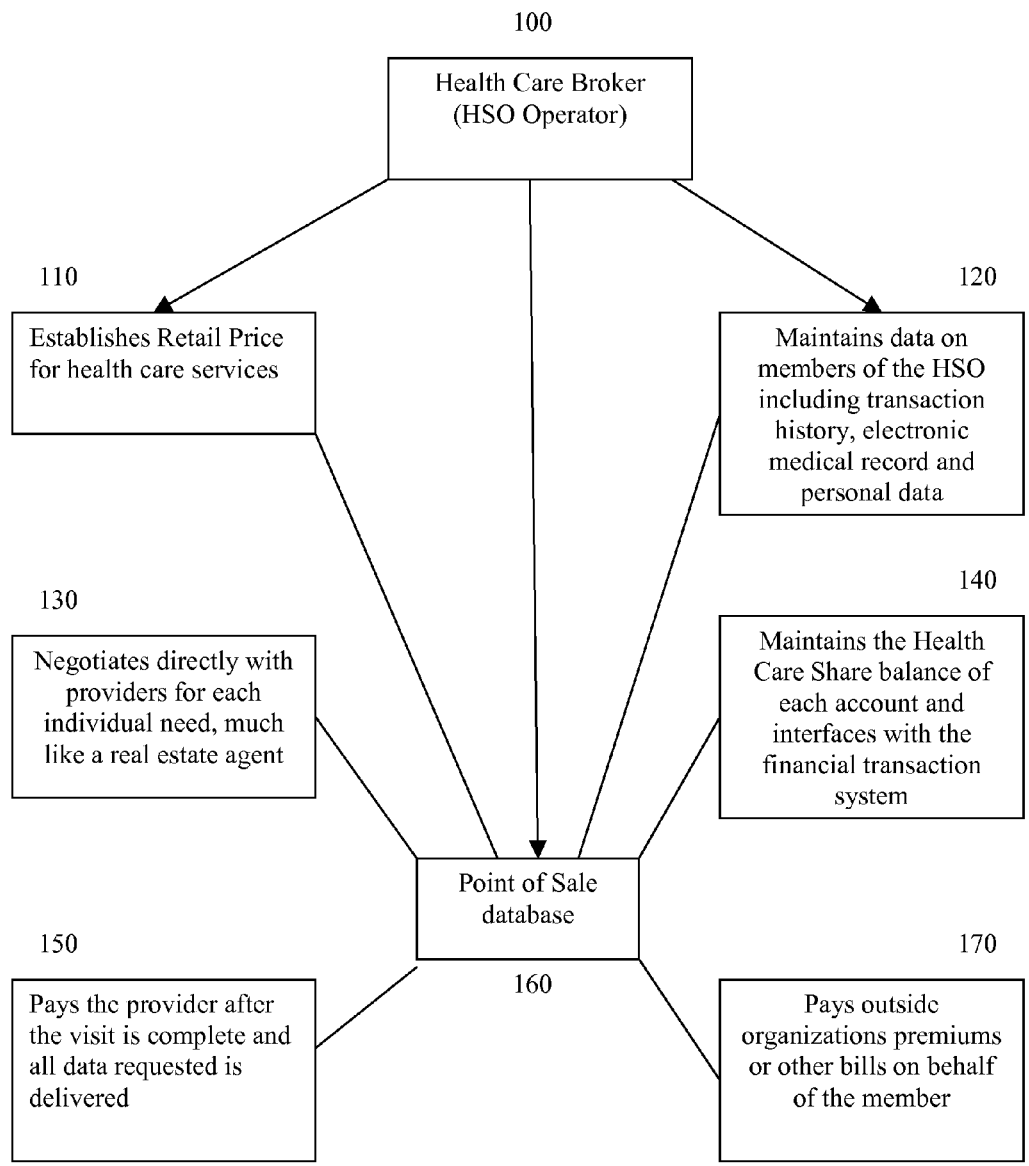
FIG. 4 is a block diagram illustrating the duties of the Health Care Broker (HSO Operator)

FIG. 4 is a block diagram illustrating the duties of the Health Care Broker (HSO Operator) 100. All activity occurs through an independent product representative or company operated call center. The broker: establishes retail price for health care services 110; maintains data on members of the HSO including transaction history, electronic medical record and personal data 120; negotiates directly with providers for each individual need, much like a real estate agent 130; maintains the Health Care Share balance of each account and interfaces with the financial transaction system 140; pays the provider after the visit is complete and all data requested is delivered 150; and pays outside organizations premiums or other bills on behalf of the member 160, all of which is logged in the point of sale database 200.

Figure 5:
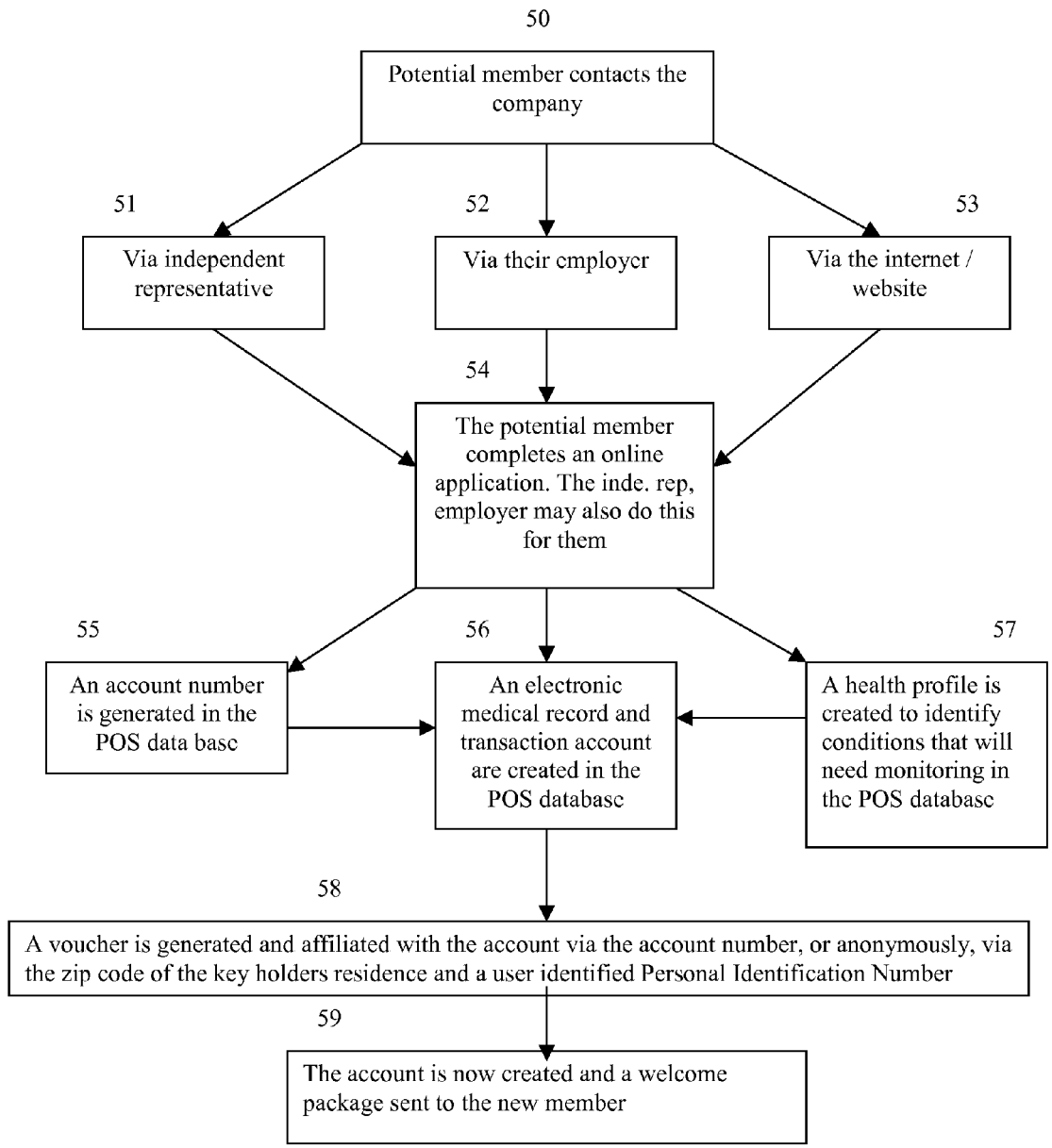
FIG. 5 is a block diagram illustrating the sequence for enrolling in the Health Security Organization.

FIG. 5 is a block diagram illustrating the sequence for enrolling in the HSO. The potential member contacts the company 50 via independent representative 51, employer 52, or website 53. The potential member completes an application 54. Then, an account number is generated in the POS database 55, an electronic medical record and transaction account are created in the POS database 56, and a health profile is created to identify conditions that will need monitoring in the POS database 57. A voucher is generated and affiliated with the account via the account number, or anonymously, via the zip code of the key holders residence and a user identified Personal Identification Number 58. Finally, the account is now created and a welcome package sent to the new member 59.

Figure 6:
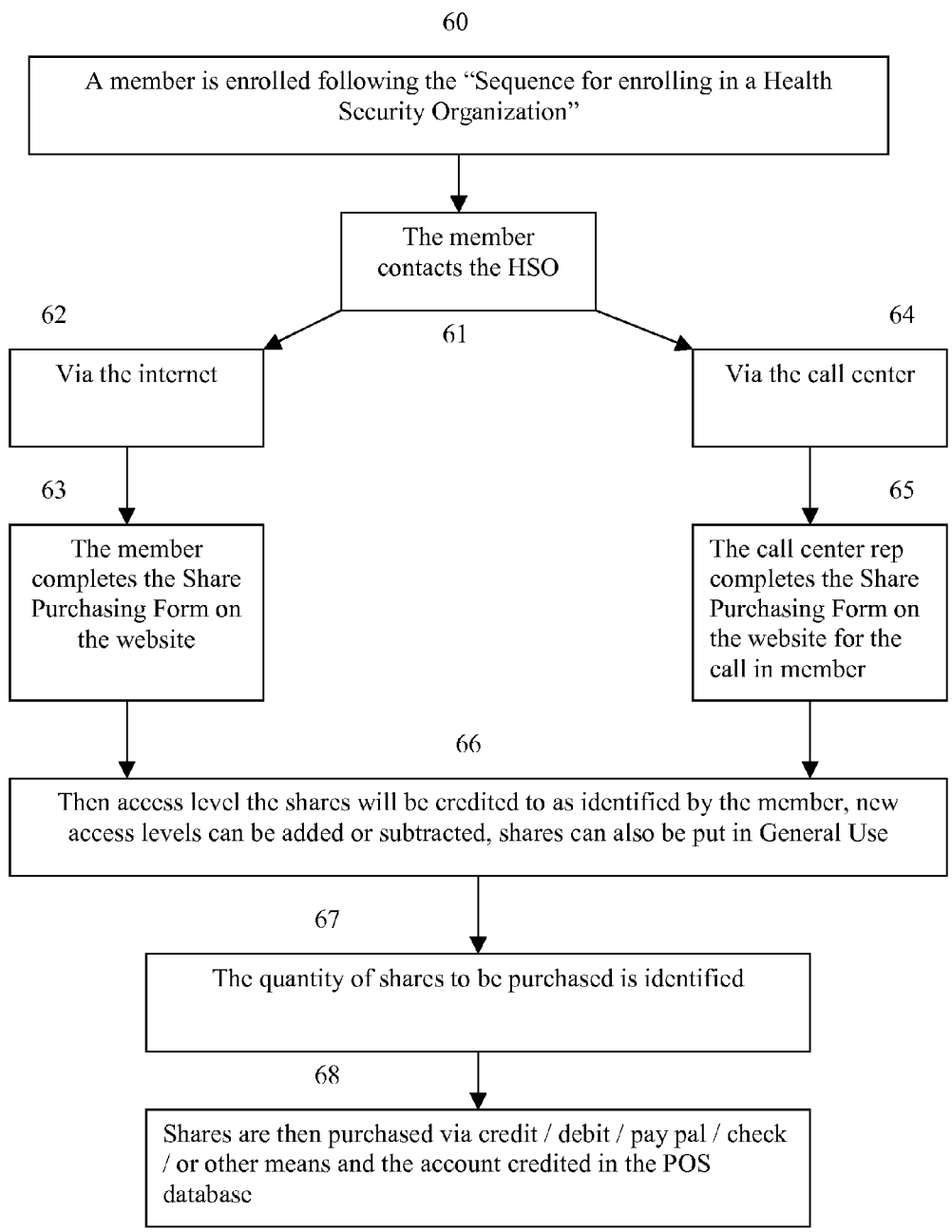
FIG. 6 is a block diagram illustrating the sequence for purchasing shares.

FIG. 6 is a block diagram illustrating the sequence for purchasing shares in the HSO. Once a member is enrolled 60, the member contacts the HSO 61 either online 62 or by phone 64. If contacting online, the member completes the Share Purchasing Form on the website 63. If via phone, the call center rep completes the Share Purchasing Form on the website for the call in member 65. From there, access level the shares will be credited to as identified by the member, new access levels can be added or subtracted, shares can also be put in General Use 66. Then, the quantity of shares to be purchased is identified 67. Shares are then purchased via credit/debit/pay pal/check/or other means and the account credited in the POS database 68.

Figure 7:
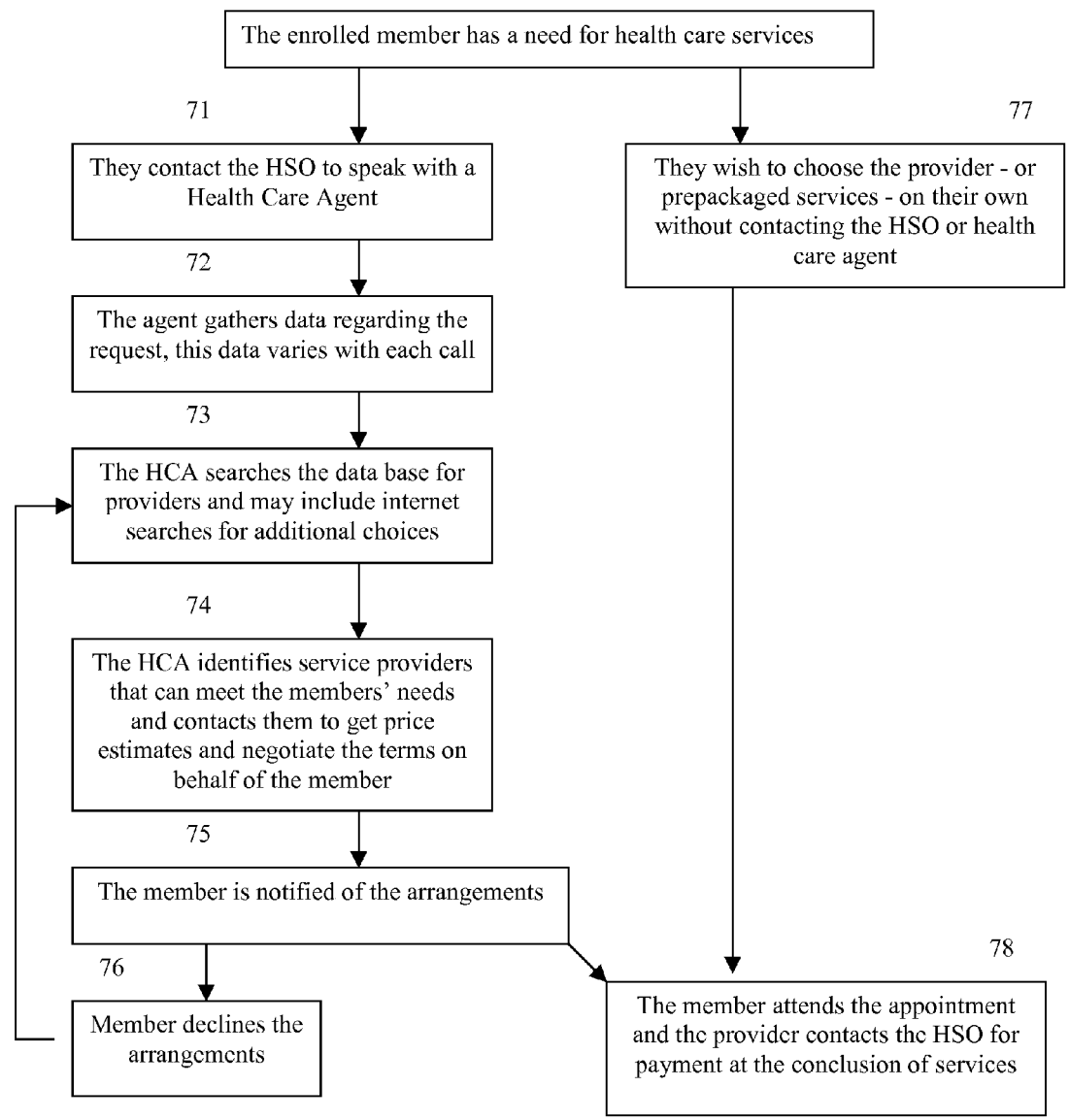
FIG. 7 is a block diagram illustrating the sequence for acquiring services.

FIG. 7 is a block diagram illustrating the sequence for acquiring services in the HSO. Once, the enrolled member has a need for health care services 70, they may either contact the HSO to speak with a Health Care Agent 71 or choose the provider on their own without contacting the HSO or health care agent 77. If they, contact the HSO, the agent gathers data regarding the request 72, searches the database for providers 73, identifies service providers that can meet the members' needs and contacts them to get price estimates and negotiate the terms on behalf of the member 74, and then notifies the member of the arrangements 75. From that point, the member may decline the arrangement and request a new search from the agent 76, or the member may attend the appointment, at which point the provider will contact the HSO for payment upon conclusion of services 78.

The member may, however, feel more comfortable choosing the provider on his or her own without contacting the HSO or health care agent 77. The member will then attend the appointment, and the provider will contact the HSO for payment upon conclusion of services 78.

Figure 8:
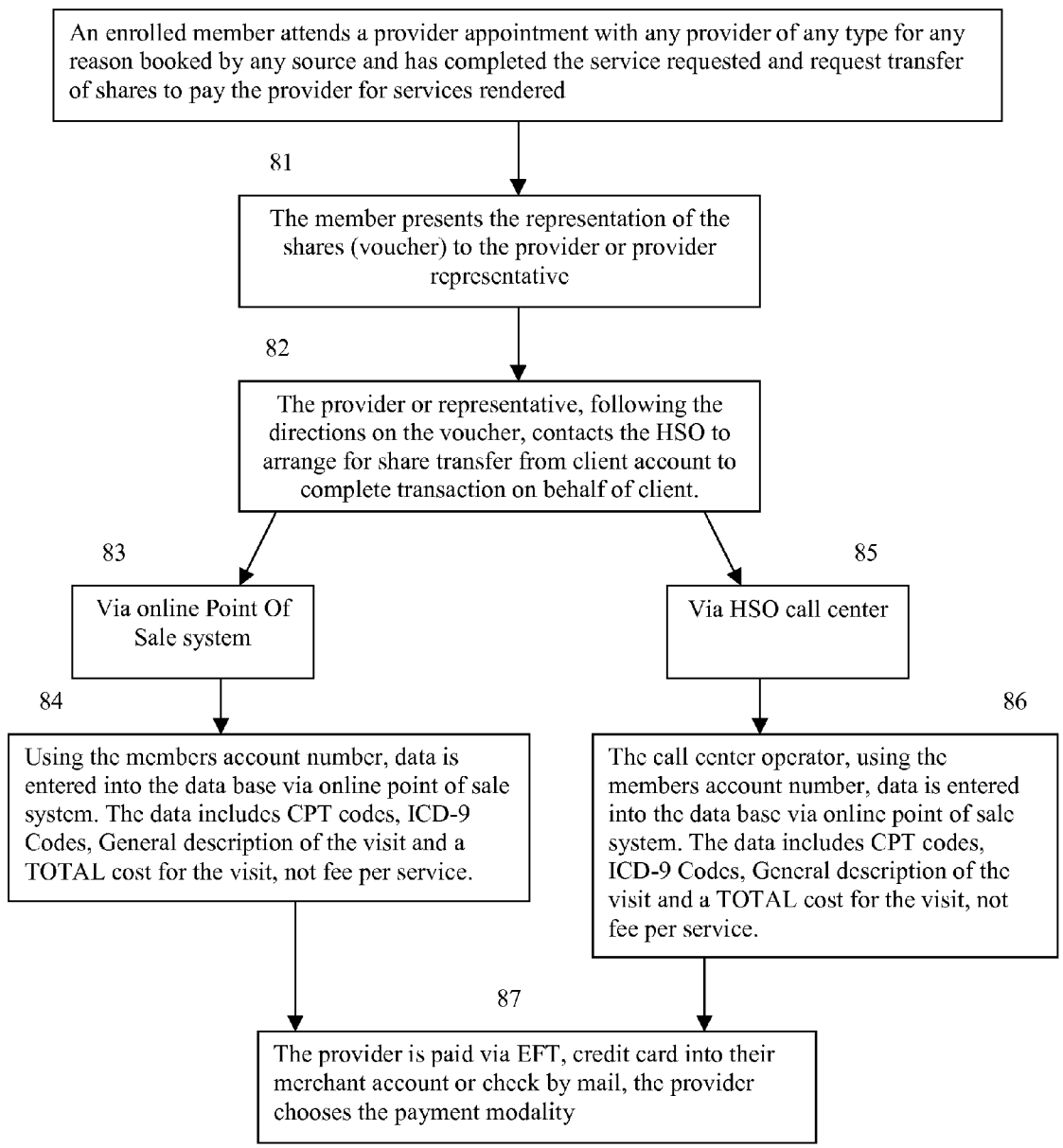
FIG. 8 is a block diagram illustrating the sequence for redeeming shares.

FIG. 8 is a block diagram illustrating the sequence for redeeming shares in the HSO. When an enrolled member attends a provider appointment with any provider of any type for any reason booked by any source and has completed the service requested and needs to pay the provider for services rendered 80, the member resents the representation of the shares (voucher) to the provider or provider representative 81. The provider follows the direction on the voucher and contacts the HSO 82 via an online Point Of Sale system 83 or over the phone to the HSO call center 85. If online, the provider uses the member's account number for identification to enter data into the database 84. The data includes CPT codes, ICD-9 Codes, General description of the visit and a TOTAL cost for the visit, not fee per service. If through the call center, the call center operator uses the member's account number for identification to enter data into the database 86. The data includes CPT codes, ICD-9 Codes, General description of the visit and a TOTAL cost for the visit, not fee per service. Finally, the provider is paid via EFT, credit card into their merchant account, or check by mail 87. The provider chooses the payment modality.

Figure 9:
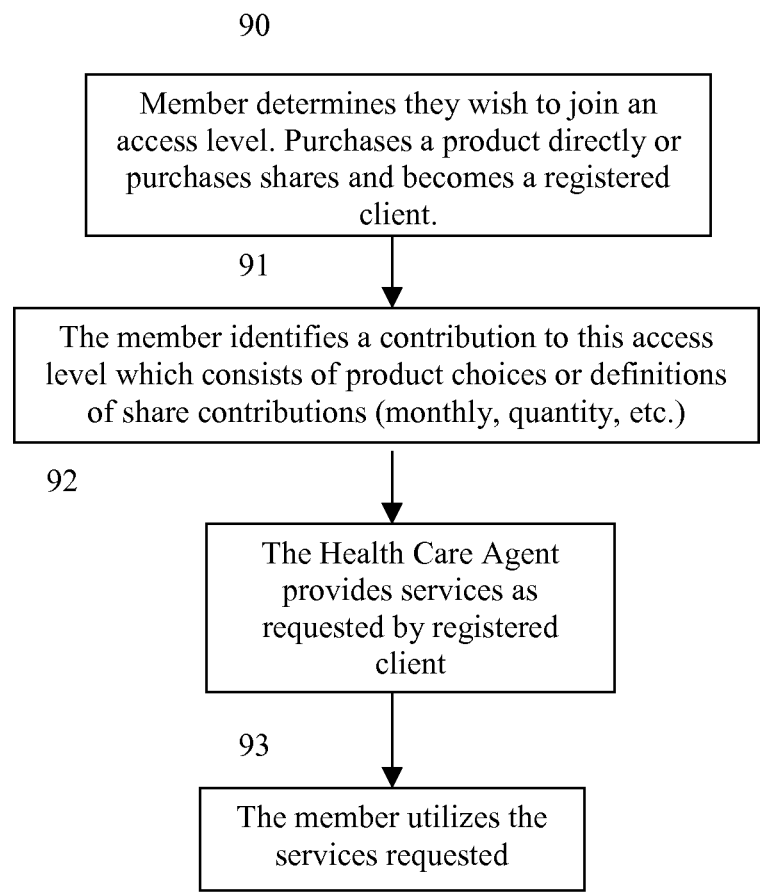
FIG. 9 is a block diagram describing the access levels.

FIG. 9 is a block diagram describing the access levels in the HSO. A member determines they wish to join an access level 90. Then, the member identifies a monthly contribution to this access level 91. The Health Care Agent assigned to the access level uses these funds to arrange specialized services for the member, including group visits, health fairs and other events 92, upon which the member attends the services as needed and desired 93.

Access levels are ways a member of the HSO can identify where they want their health care shares to be represented. By choosing access levels they are assigning their shares to different service buying efforts that include bulk buying of services, group visits, pre paid visits, health fairs and other methods of achieving savings on anticipated health care needs. An example would be a member that has diabetes, and assigns 100 a month to the diabetes access level. By doing this they have requested participation in a care coordination effort that includes all the standard services of the HSO and more direct services for their specific condition, arranged locally, to better serve their needs both financially and medically.

Figure 10:
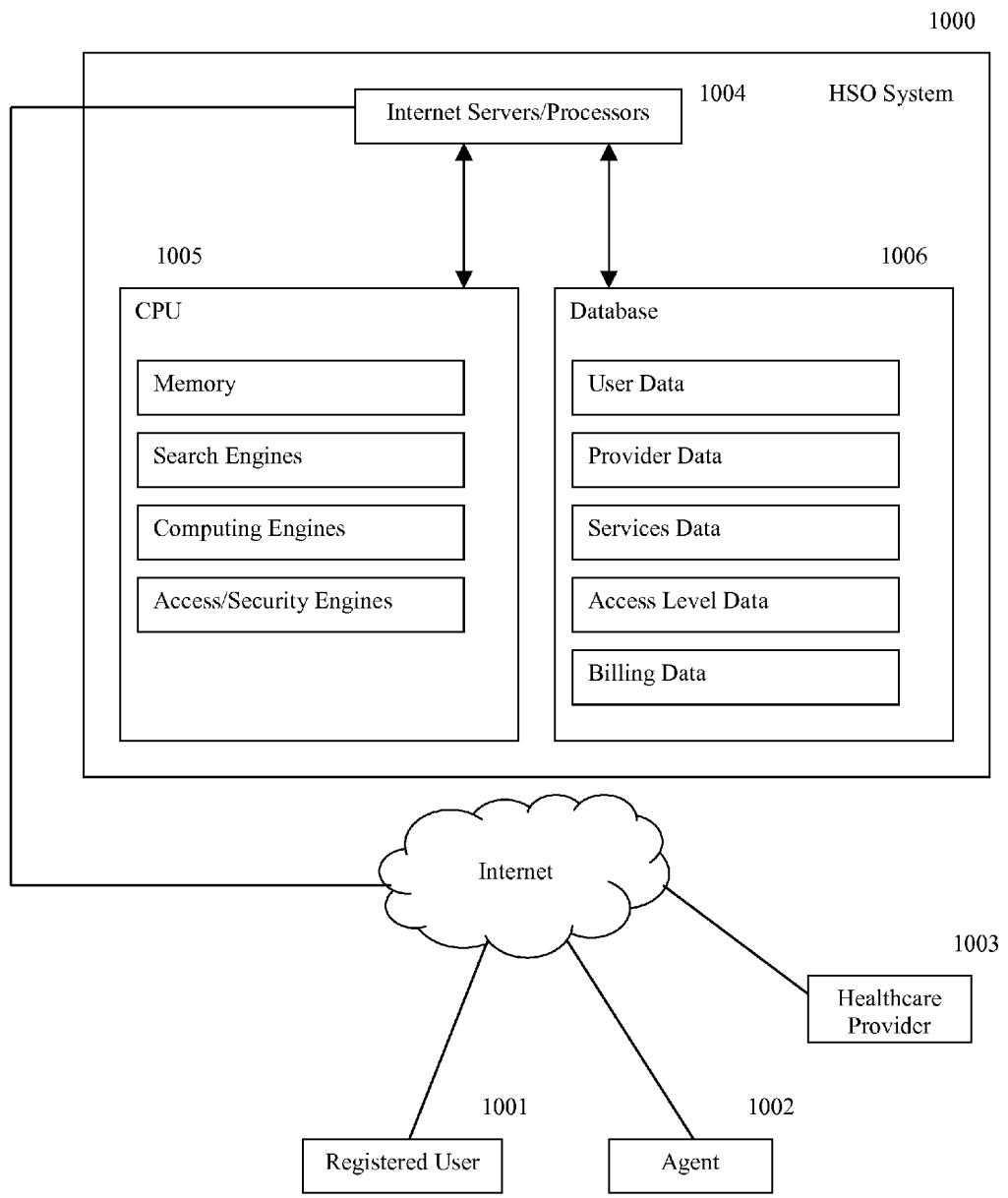
FIG. 10 is a block diagram describing the HSO system and its components.

FIG. 10 is a block diagram illustrating the HSO system and its components. When it's necessary to modify an account, either by a user, provider, or a representative of the HSO, an individual will access the HSO system 1000 to administer changes. A registered user 1001, agent 1002, or healthcare provider 1003 can access the HSO system 1000 via any electronic device with access to the internet or similar communication network. From there, an individual can access their respective data on the servers 1004. These servers are comprised of hardware and software required to operate key function known to those of ordinary skill in the art. The operating functions 1005 is comprised of elements including but not limited to: one or multiple CPUs; RAM and ROM memory; search engines; computing engines; access/security engines. The database 1006 and its functions are controlled and recorded by the server and its hardware. The database is comprised of information including but not limited to: user data; provider data; available products and services data; access level data; bundled services data; billing and accounting data. It is known to those of ordinary skill in the art that this HSO system may be comprised of one or many processors, databases, etc. This system preferably uses the public internet as a primary means of communication between it and other individual parties via an internet enabled device. However, this is not a limiting factor as this system can just as easily be implemented over a virtual private network or other. The intent is to offer streamlined access between multiple types of entities and the HSO system.

Figure 11:
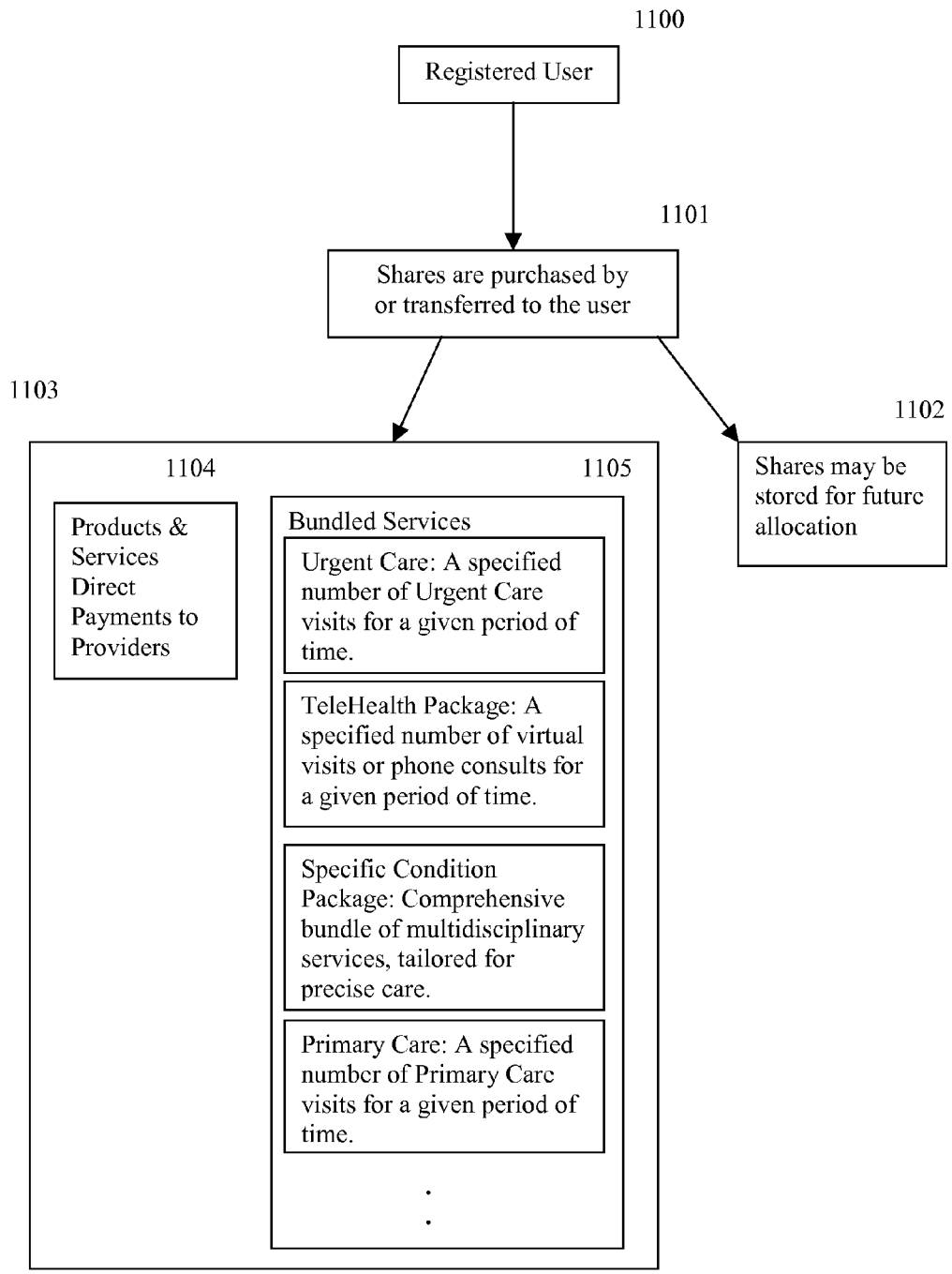
FIG. 11 is a block diagram describing the process for purchasing products and services by the user using shares.

FIG. 11 is a block diagram describing the process for purchasing products and services by the user using shares. After completing the registration process, a user 1100 can acquire shares 1101 by purchasing them or having them transferred or gifted to them by an employer, family member, etc. Once a registered user has shares, they may wish to store them in their accounts for future allocation 1102. A user may wish to transfer or gift his shares, or use them for themselves. Furthermore, a user may use their shares 1103. Generally speaking, there are two basic ways to use shares. A user may choose to transfer shares to currency as payment to provider directly 1104 for products or services. The use of shares in this manner is optimum for unexpected or uncalculated need of services. The shares are recorded as a product purchase and booked to the client. They can then be redeemed at any point in time at the direction of the client. The amount of services they receive for the redemption is determined at that point in time. Another general option for using shares is to purchase bundled services 1105. These bundled services are a unique feature in this field. Bundled services are exemplified but not limited to these embodiments: a specified number of urgent care visits for a given period of time; a specified number of "virtual visits" or phone consults for a given period of time; a comprehensive bundle of multidisciplinary services tailored for precise care (i.e. cancer, diabetes, heart disease, etc.); a specified number of primary care visits for a given period of time. The primary intent of bundled services is to provide the user with tailored, interdisciplinary care for an expected cost. Furthermore, bundled services offer the providers a way of anticipating the complete cost of care while being assured they will receive immediate payment for said care. An interdisciplinary bundle is not limited to any specific condition, but rather can be tailored by the HSO for any given need.

The skilled artisan will appreciate that the apparatus and method of providing an exemplary HSO method as disclosed herein may easily be adapted for use in other fields of professional service such as the provision of legal and accounting services, and/or wherever it may be desirable to permit market forces to impact the transactional cost of providing services. While particular exemplary embodiments of the HSO acquisition and transaction method have been illustrated and described, it will be obvious to one of ordinary skill in the art that various other changes and modifications can be made without departing form the spirit and scope of the invention. The appended claims are therefore intended to cover all such changes and modifications.

The invention claimed is:

1. An online Health Security Organization (HSO) system implemented over a publicly accessible communications network, said system enabling one or more healthcare providers to offer healthcare services and products to one or more users connected to said network, said system comprising:

an HSO computer system connected to a publicly accessible communications network;

a computer-readable storage device connected to said computer system for storing one or more system administrated databases, including at least one system administrated database containing information concerning registered users, at least one system administrated database containing information concerning registered service providers;

a mechanism for controlling said computer system for maintaining said system administrated databases and for causing the computer system to provide an interactive online healthcare services transaction processing website accessible via said network and which serves as a comprehensive healthcare marketplace for vending and obtaining healthcare services and products between said user and provider;

said system further comprising the use of Health Care Shares of a specific level of access, represented by a voucher for direct payment to the service provider, wherein said access levels are a specific classification and identity for all health care services; and wherein the Health Care Shares real value is a function of the finite number of health care service that are available at any given moment in time.

2. The system of claim 1 wherein the communications network is composed of a digital communications network between a Point of Sale system and a system administrated database.

3. The system of claim 2, wherein the system administrated database enables retention and retrieval of all consumer data.

4. The system of claim 1 wherein the registered user is a shareholder.

5. The system of claim 1 wherein the communications network is a singular, online health care specific Point of Sale system that aggregates: the total number of Health Care Shares available; the total number of Health Care Shares the consumer owns, has used, and has purchased; a transaction history for the consumer; an electronic medical record for the consumer; a portal for transactions for the service provider; a list of all ICD-9 codes and CPT codes; a list of all service providers that have completed a transaction; a list of all service providers performance records; and a list of all service providers charges from past transactions.

6. A method of exchanging shares for healthcare services and products via Health Security Organization (HSO) over a publicly accessible communications network as performed by a computer system, comprising:

providing an interactive Internet accessible Health Security Organization (HSO) transaction processing website hosted by at least one computer of said server computer system that is connected to said communications network, said website enabling a financial transaction between a pinnacle monitor of the system or other service professional and a service provider on behalf of a registered user to obtain proffered healthcare products or services; and providing dynamic information to all parties involved in the financial transaction by using a singular, online health care specific Point of Sale system that aggregates:

a total number of Health Care Shares available;

a total number of Health Care Shares the consumer owns, has used, and has purchased;

a transaction history for the consumer; an electronic medical record for the consumer; a portal for transactions for the service provider; a list of all ICD-9 codes and CPT codes;

a list of all service providers that have completed a transaction; a list of all service providers performance records; and a list of all service providers charges from past transactions; and wherein the financial transaction is made by converting the Health Care Shares of a specific level of access, represented by a voucher for direct payment to the service provider, wherein said access levels are a specific classification and identity for all health care services;

wherein the Health Care Shares real value is a function of the finite number of health care service that are available at any given moment in time.

7. The method of claim 6 wherein the registered user is a shareholder.

8. The method of claim 6 wherein the financial transaction is made by converting the Health Care Shares of a specific level of access, represented by a voucher for the purchase of bundled services.

9. The method of claim 6 wherein a bundles service is a comprehensive bundle of multidisciplinary healthcare services, tailored for precise care of a specific medical condition.

* * * * *